United States Patent
Oshida et al.

(10) Patent No.: US 7,220,779 B2
(45) Date of Patent: May 22, 2007

(54) SWINE GROWTH PROMOTERS AND METHOD OF PROMOTING SWINE GROWTH

(75) Inventors: Toshio Oshida, Sagamihara (JP); Tohru Tanaka, Minato-ku (JP)

(73) Assignee: Cosmo Oil Co., Ltd., Tokyo (JP)

( * ) Notice: Subject to any disclaimer, the term of this patent is extended or adjusted under 35 U.S.C. 154(b) by 402 days.

(21) Appl. No.: 10/485,368

(22) PCT Filed: Jul. 23, 2002

(86) PCT No.: PCT/JP02/07443

§ 371 (c)(1), (2), (4) Date: Jan. 30, 2004

(87) PCT Pub. No.: WO03/011275

PCT Pub. Date: Feb. 13, 2003

(65) Prior Publication Data

US 2004/0234555 A1 Nov. 25, 2004

(30) Foreign Application Priority Data

Jul. 31, 2001 (JP) .............................. 2001-231351

(51) Int. Cl.
*A61K 31/195* (2006.01)

(52) U.S. Cl. ...................... 514/563; 514/553; 514/557; 514/561

(58) Field of Classification Search ..................... None
See application file for complete search history.

(56) References Cited

U.S. PATENT DOCUMENTS 5,298,482 A * 3/1994 Tanaka et al. .............. 504/320

FOREIGN PATENT DOCUMENTS

| EP | 1 153 546 A1 | 11/2001 |
| JP | 11-171852 A | 6/1999 |
| WO | WO 97/41855 A1 | 11/1997 |
| WO | WO 00/71089 A | 11/2000 |

OTHER PUBLICATIONS

Jenkins et al, Eur J Endovas Surg, 1998, vol. 16, pp. 284-291.*

* cited by examiner

*Primary Examiner*—Leon B. Lankford, Jr.
*Assistant Examiner*—Allison M. Ford
(74) *Attorney, Agent, or Firm*—Sughrue Mion, PLLC

(57) ABSTRACT

A pig growth enhancer, which comprises, as an active ingredient, at least one compound selected from 5-aminolevulinic acid, a derivative thereof and a salt thereof, and a method for enhancing pig growth, which comprises administering the growth enhancer to a pig.

4 Claims, No Drawings

SWINE GROWTH PROMOTERS AND METHOD OF PROMOTING SWINE GROWTH

TECHNICAL FIELD

The present invention relates to a pig growth enhancer and a method for enhancing pig growth using the same.

BACKGROUND OF THE INVENTION

Pigs are useful domestic animals which are raised for edible meat, show quick growth and have high conversation rate of grains into meat. However, being quick in growth, they show symptoms such as physiologic anemia particularly at their early stage of growth, frequently causing inhibition of growth and onset of diseases. As a countermeasure, administration of drugs (iron preparations) and administration of various medicines for promoting nutrition are carried out but with no sufficient results. Particularly, injection of iron-dextran and oral administration of iron sulfate and iron fumarate are carried out for the purpose of improving physiologic anemia symptoms at the early stage of growth.

However, although administration of iron preparations has a certain effect in improving physiologic anemia and preventing the disease, it is not sufficient in terms of enhancing the growth. In addition, the oral administration of iron components has problems in that their absorption in the intestines is poor and they spoil taste of feed, and the injection, on the other hand, has problems in that it puts a stress on pigs and takes plenty of time in comparison with oral administration.

It is known that 5-aminolevulinic acids have a herbicide action (JP-A-61-502814, JP-A-4-9360), an insecticide action (JP-A-2-138201), a sensitizing action on photo-dynamic cancer therapy, a plant growth enhancing action (Japanese Patent No. 2,613,136) and the like, but their possibility of enhancing growth of pigs is not known.

DISCLOSURE OF THE INVENTION

The present invention contemplates providing a pig growth enhancer which has high growth enhancing effect, shows good absorption even in the case of its oral administration and does not spoil taste of feed, and a method for enhancing pig growth.

The present invention relates to the following (1) to (3).
(1) A pig growth enhancer, which comprises, as an active ingredient, at least one compound selected from 5-aminolevulinic acid, a derivative thereof and a salt thereof
(2) The pig growth enhancer according to (1), which further comprises an iron component.
(3) A method for enhancing pig growth, which comprises administering the growth enhancer according to (1) or (2) to a pig.

BEST MODE FOR CARRYING OUT THE INVENTION

The 5-aminolevulinic acid, a derivative thereof and a salt thereof as the active ingredients of the pig growth enhancer of the present invention are known compounds. Among these, examples of the derivatives of 5-aminolevulinic acid include 5-aminolevulinic acid ester, N-acyl-5-aminolevulinic acid, N-acyl-5-aminolevulinic acid ester and the like.

Examples of the 5-aminolevulinic acid ester include alkyl esters which have an alkyl group of 1 to 24 carbon atoms having a straight chain, branched chain or cyclic structure which may have a substituent. Examples of the substituent which may be possessed by the alkyl group include a hydroxyl group, an alkoxy group, a phenyl group and the like. Preferred examples of the alkyl group which may have such a substituent include a methyl group, an ethyl group, an n-propyl group, an isopropyl group, an n-pentyl group, an n-hexyl group, a cyclohexyl group, an n-heptyl group, an n-octyl group, an n-nonyl group, an n-dodecyl group, an n-hexadecyl group, a benzyl group, a phenetyl group, a 3-phenylpropyl group, a hydroxyethyl group, an ethoxyethyl group and the like.

Examples of the N-acyl-5-aminolevulinic acid include compounds resulting from the acylation of the amino group of 5-aminolevulinic acid with, e.g., an acyl group having from 1 to 24 carbon atoms such as an alkanoyl group, an aromatic acyl group or a benzyloxycarbonyl group. Examples of preferred acyl groups include an acetyl group, an n-propanoyl group, an n-butanoyl group, an n-pentanoyl group, an n-hexanoyl group, n-nonanoyl group, benzyloxycarbonyl group and the like.

Examples of the N-acyl-5-aminolevulinic acid ester include those which have the above ester and acyl groups. Preferred are combinations of a methyl ester group with a formyl group, a methyl ester group with an acetyl group, a methyl ester group with an n-propanoyl group, a methyl ester group with an n-butanoyl group, an ethyl ester group with a formyl group, an ethyl ester group with an acetyl group, an ethyl ester group with an n-propanoyl group and an ethyl ester group with an n-butanoyl group.

Examples of the salts of 5-aminolevulinic acid or derivatives thereof include acid addition salts such as hydrochloride, hydrobromide, hydroiodide, phosphate, nitrate, sulfate, acetate, propionate, toluenesulfonate, succinate, oxalate, lactate, tartarate, fumarate, maleate and malate; metal salts such as sodium salt, potassium salt and calcium salt; ammonium salts; alkyl ammonium salts; and the like. Also, these salts are used as aqueous solution or powder when used, and their activity is identical to the case of 5-aminolevulinic acid.

The above 5-aminolevulinic acid, derivatives thereof or salts thereof may be in the form of hydrates or solvates, and any one of them can be used alone or by optionally combining two or more of them.

The 5-aminolevulinic acid or a salt thereof can be produced by any one of the methods of chemical synthesis, microbial production and enzymatic production. Also, the above derivatives of 5-aminolevulinic acid or salts thereof can be produced for example by the usually known chemical synthesis methods described in JP-A-4-9360 and the like. The products by microorganisms or enzymes and crude products by chemical synthesis methods can be used as such without carrying out separation and purification with the proviso that they do not contain substances which are toxic for the growth of pigs.

The pig growth enhancer of the present invention can synergistically improve its growth enhancing effect by further formulating an iron component. Any material which contains iron and does not have bad influence on pig growth can be used as such an iron component. Examples include metallic iron, and iron compounds such as iron chloride, iron nitrate, iron sulfate, iron oxalate, iron succinate, iron fumarate, iron citrate, ferric ammonium citrate, EDTA iron, dextran iron, dextrin iron, iron oxide, heme iron, gleptoferron, choline iron citrate, peptide iron, DL-threonine iron and iron tartarate, and these iron components can be used alone or as a combination of two or more.

If necessary, other component or carrier such as other drug efficacy component or medicament for promoting nutrition can be added to the growth enhancer of the present invention.

Dosage form of the growth enhancer of the present invention may be either powders or solutions, and they can be produced in accordance with the usual way optionally using a solvent, a dispersion medium, an excipient and the like.

When the growth enhancer of the present invention is prepared as an aqueous solution, it is necessary to pay attention such that the aqueous solution does not become alkaline, in order to prevent degradation of 5-aminolevulinic acid, a derivative thereof or a salt thereof as the active ingredient. In case that it becomes alkaline, degradation of the active ingredient can be prevented by removing oxygen.

The pig growth enhancing method of the present invention can be effected so far as it can enhance growth of pigs by administering the preparation thereto, and though the method for using the preparation is not particularly limited, its preferred embodiment is shown below.

The breed of pigs to be treated by the growth enhancing method using the preparation is not particularly limited, its preferred examples include Landrace, Large Yorkshire, Duroc, Berkshire, Umeyama pig and the like.

The preparation can be used at any stage of the growth, but in the case of a piglet, earlier stage of the growth under physiologic anemia condition is effective. In addition, its administration to a pregnant mother sow is effective for health control of the mother sow and also effective for growth enhancement of the breeding piglets.

Although administration method of the growth enhancer of the present invention to pigs is not particularly limited, oral administration and injection administration can be exemplified, of which oral administration is preferable.

Although the preparation shows sufficient effect by its single administration, it can be administered two or more times in order to further strengthen the effect. The effect per provided preparation is higher in the case of two or more administrations, and its everyday administration in small portions by adding it to feed, drinking water, milk and the like is an efficient using method.

Single dose of the preparation per 1 kg pig body weight is preferably from 1 µg to 1 g, more preferably from 1 µg to 100 mg, particularly preferably from 1 µg to 50 mg, based on 5-aminolevulinic acid hydrochloride. Regarding the dose of the preparation, larger amount is necessary as the growth becomes vigorous stage and the administration frequency becomes less. Its administration exceeding the suitable range is not desirable, because not only it is uneconomical but also it has a possibility of causing sunlight damages on pigs.

When an iron preparation is jointly used, it may be used simultaneously or used separately. Its using method may be the same as the using method of usual iron preparations.

It is considered that a reaction mechanism in which 5-aminolevulinic acid as the active ingredient of the preparation is converted into a heme in the living body, thereby reinforcing hemoglobin and alleviating symptoms of physiologic anemia, is one of the reasons for the preparation to show pig growth enhancing effect, but the increase in protein concentration in sera and the significant growth enhancement cannot be explained by this reason alone.

Next, the present invention is described in detail with reference to examples, but the present invention is not limited to these examples.

EXAMPLE 1

Using Large Yorkshire piglets bone during a period of from September through October in 2000, and on the third day after birth, 50 mg of 5-aminolevulinic acid hydrochloride per 1 kg body weight was dissolved in 2 ml of distilled water and orally administered to an "ALA plot", conventional iron-dextran (manufactured by Takeda Chemical Industries) was administered to an "iron plot" by intramuscular injection, and both of them were carried out in an "ALA+iron plot". Also, these administrations were not carried out in a "no treatment plot".

Thereafter, usual management was carried out, feeding was started on the 14th day after birth, and body weights were measured and blood samples were collected on the 21st day after birth to carry out inspections in accordance with usual way. Also, body weights were measured at the time of shipping after about 6 months, and the number of days reaching a shipping body weight criterion of 110 kg (required days for 110 kg) was calculated. The tests were carried out using 12 animals in each plot, and the values were calculated as average values by excluding pigs which came off the test due to a disease and the like.

The results of examination carried out on the 21st day after birth are shown in Table 1, and the results of examination carried out about 6 months after birth in Table 2.

TABLE 1

|  | RBC | Hb | Ht | TP | Fe | $B_{12}$ | Body weight |
|---|---|---|---|---|---|---|---|
| Non-treated plot | 4.25 | 7.5 | 27.4 | 5.2 | 46 | 201 | 221 |
| Iron plot | 4.72 | 8.4 | 31.4 | 6.0 | 149 | 226 | 234 |
| ALA plot | 4.37 | 8.5 | 30.5 | 5.8 | 44 | 240 | 233 |
| ALA + iron plot | 5.76 | 9.2 | 35.5 | 5.9 | 153 | 272 | 289 |

Notes:
RBC: the number of erythrocytes in whole blood sample ($\times 10^4/\mu l$)
Hb: hemoglobin concentration in whole blood sample (g/dl)
Ht: blood cell volume ratio in whole blood sample (%)
TP: total serum protein concentration in serum (g/dl)
Fe: serum iron concentration in serum (µg/dl)
$B_{12}$: vitamin $B_{12}$ concentration in serum (pg/ml)
Body weight: relative value (%) to 100 at the time of the commencement of the test on the 3rd day after birth As is evident from Table 1, it can be understood that the administration of ALA is useful in improving growth of piglets and blood indexes such as physiologic anemia. It is effective for hemoglobin concentration, blood cell volume ratio, total serum protein concentration and vitamin $B_{12}$, particularly vitamin $B_{12}$. Joint use of the iron preparation further improved the effects, particularly on the increase in body weight.

Although not shown in the table, the pig which came off the test plots due to a disease and the like until on the 21st day after birth was 2 head in the non-treated plot and 1 head in the iron plot, and not found in the ALA plot and ALA+iron plot. It can be considered that this is due to the effect of ALA administration to enhance health of piglets.

TABLE 2

|  | Required days for 110 kg* | Frequency of disease onset |
| --- | --- | --- |
| Non-treated plot | 199 | 3 |
| Iron plot | 192 | 2 |
| ALA plot | 183 | 0 |
| ALA + iron plot | 175 | 0 |

*The number of days reaching a shipping body weight criterion of 110 kg. This is calculated in accordance with the following formula.
DG (daily gain; kg/day) = shipping body weight (kg) ÷ raised days (day)
Required days for 110 kg (day) = 110 (kg) ÷ DG (kg/day)

As is evident from Table 2, administration of ALA enhances growth, and its combination with iron preparation is more effective and can sharply shorten the number of days until shipping. In addition, one head of pig came off the test system due to a disease in and after the 21st day in each of the non-treated plot and iron plot, but diseases were not found in the ALA plot and ALA+iron plot.

EXAMPLE 2

Using piglets born during a period of from October through November in 2000, feeding was carried out on the 14th day after their birth. Their growth was observed in a plot provided with a general feed, a plot in which 10 mg per 1 kg feed of 5-aminolevulinic acid hydrochloride was added to the general feed (ALA plot) and a plot in which 10 mg of ferric ammonium citrate (Brawn) was further added per 1 kg of the feed (ALA+iron plot), to find the required days for 110 kg as shown in Table 3. In this case, the test was carried out using 10 head in each plot, and the average values were calculated.

TABLE 3

|  | Required days for 110 kg |
| --- | --- |
| Non-treated plot | 198 |
| ALA plot | 172 |
| ALA + iron plot | 171 |

As is evident from Table 3, the growth was markedly enhanced in each of the ALA plot and ALA+iron plot, showing effective results. In this connection, pigs came off the test due to diseases were not found in Example 2.

INDUSTRIAL APPLICABILITY

Since health of pigs can be maintained and their growth can be enhanced by the pig growth enhancer of the invention and the pig growth enhancing method using the same, economical effects are great for hog raisers.

The invention claimed is:

1. A method for enhancing pig growth, which comprises administering to a pig an effective amount of a growth enhancer comprising at least one compound selected from 5-aminolevulinic acid, 5-aminolevulinic acid ester, N-acyl-5-aminolevulinic acid or N-acyl-5-aminolevulinic acid ester or a salt thereof, wherein the effective amount of the growth enhancer is given in a single dose which is 1 μg to 50 mg per 1 kg pig body weight.

2. The method according to claim 1, wherein the growth enhancer further comprises an iron component.

3. A method for enhancing pig growth, which comprises administering to a pig an effective amount of a growth enhancer comprising at least one compound selected from 5-aminolevulinic acid, 5-aminolevulinic acid ester, N-acyl-5-aminolevulinic acid or N-acyl-5-aminolevulinic acid ester or a salt thereof, wherein said administering is oral administering.

4. The method according to claim 3, wherein the growth enhancer further comprises an iron component.

* * * * *